(12) United States Patent
Wolf, Jr. et al.

(10) Patent No.: US 6,800,432 B1
(45) Date of Patent: Oct. 5, 2004

(54) APPARATUS AND METHOD FOR INACTIVATING VIRAL CONTAMINANTS IN BODY FLUIDS

(75) Inventors: Ludwig Wolf, Jr., Barrington, IL (US); William Bratten, Lake Villa, IL (US); John Foley, Wheeling, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/675,511

(22) Filed: Sep. 29, 2000

Related U.S. Application Data

(63) Continuation of application No. 08/350,398, filed on Dec. 6, 1994, now abandoned.

(51) Int. Cl.[7] .............................. A01N 1/02; C12N 7/06
(52) U.S. Cl. ........................................... 435/2; 435/238
(58) Field of Search ...................... 435/2, 238

(56) References Cited

U.S. PATENT DOCUMENTS

| | | |
|---|---|---|
| 2,308,516 A | 1/1943 | Knott |
| 4,181,128 A | 1/1980 | Swartz |
| 4,321,919 A | 3/1982 | Edelson |
| 4,398,906 A | 8/1983 | Edelson |
| 4,402,318 A | 9/1983 | Swartz |
| 4,428,744 A | 1/1984 | Edelson |
| 4,456,512 A | 6/1984 | Bieler et al. |
| 4,573,962 A | 3/1986 | Troutner |
| 4,612,007 A | 9/1986 | Edelson |
| 4,613,322 A | 9/1986 | Edelson |
| 4,683,889 A | 8/1987 | Edelson |
| 4,684,521 A | 8/1987 | Edelson |
| 4,705,498 A | 11/1987 | Goss |
| 4,708,715 A | 11/1987 | Troutner et al. |
| 4,726,949 A | 2/1988 | Miripol et al. |
| 4,727,027 A | 2/1988 | Wiesehahn et al. |
| 4,737,140 A | 4/1988 | Lee et al. |
| 4,769,131 A | 9/1988 | Noll et al. |
| 4,775,625 A | 10/1988 | Sieber |
| 4,776,267 A | 10/1988 | Harris |
| 4,822,335 A | 4/1989 | Kawai et al. |
| 4,831,268 A | 5/1989 | Fisch et al. |
| 4,838,852 A | 6/1989 | Edelson et al. |
| 4,878,891 A | 11/1989 | Judy et al. |
| 4,889,129 A | 12/1989 | Dougherty et al. |
| 4,915,683 A | 4/1990 | Sieber |
| 4,921,473 A | 5/1990 | Lee et al. |
| 4,944,883 A | 7/1990 | Schoendorfer et al. |
| 4,950,225 A | 8/1990 | Davidner et al. |
| 4,950,665 A | 8/1990 | Floyd |
| 4,983,307 A | 1/1991 | Nesathurai |
| 5,030,200 A | 7/1991 | Judy et al. |
| 5,032,241 A | 7/1991 | Robertson et al. |
| 5,069,885 A | 12/1991 | Ritchie |
| 5,078,673 A | 1/1992 | Abrams |
| 5,445,629 A * | 8/1995 | Debrauwere et al. |
| 6,207,107 B1 * | 3/2001 | Debrauwere et al. |

FOREIGN PATENT DOCUMENTS

| | | |
|---|---|---|
| DE | 9102709 | 5/1991 |
| EP | 0 138 489 | 4/1985 |
| EP | 0 240 149 | 10/1987 |
| WO | 90/13334 | 11/1990 |

OTHER PUBLICATIONS

Webster's New World Dictionary, Third College Edition, p. 520 (1988).*

Rock et al., "Incorporation of plasticizer into red cells during storage", Transfusion 24 (6): 493–8 (1984).*

Dodd et al., "Inactivation of Viruses in Platelet Suspensions that Retain Their In Vitro Characteristics: Comparison of Psoralen–Ultraviolet A and Merocyanine 540–Visible Light Methods," Transfusion, vol. 31, No. 6, 1991, pp. 483–490.

Heinmets et al., "Inactivation of Viruses in Plasma by Photsensitized Oxidation", Walter Reed Army Institute of Research, Nov. 1955, pp. 1–16.

"High Power T–4 (12.7 mm) TS AlGaAs Red Lamp", Hewlett Packard publication, Feb. 1990.

Lambrecht et al., "Photoinactivation of Viruses in Human Fresh Plasma by Phenothiazine Dyes in Combination with Visible Light", Vox. Sang., vol. 60, 1991, pp. 207–213.

Neyndorff et al., "Development of a Model to Demonstrate Photosensitizer–Mediated Viral Inactivation in Blood", Transfusion, vol. 30, No. 6, 1990, pp. 485–490.

Wallvik et al., "Platelet Concentrates Stored at 22 C Need Oxygen", Vox. Sang., vol. 45, 1983, pp. 303–311.

Matthews et al., "Photodynamic Therapy of Viral Contaminants with Potential for Blood Banking Applications", Transfusion, vol. 28, No. 1, 1988, pp. 81–83.

Mohr et al., "Virus Inactivated Single–Donor Fresh Plasma Preparations", Infusionstherapie, vol. 19, 1992, pp. 79–83.

* cited by examiner

Primary Examiner—Irene Marx
(74) Attorney, Agent, or Firm—M. C. Mayo; F. C. Kowalik; Bell, Boyd & Lloyd

(57) ABSTRACT

A method and apparatus for inactivating viruses in a body fluid. A mixture including a therapeutically effective amount of methylene blue and an amount of a body fluid is formed in a container under sterile conditions and then the container is irradiated with a light field of a suitable intensity and wavelength for activating the methylene blue for a time sufficient to inactivate viruses in the mixture. The mixture is maintained in a substantially static state within the container.

18 Claims, 2 Drawing Sheets

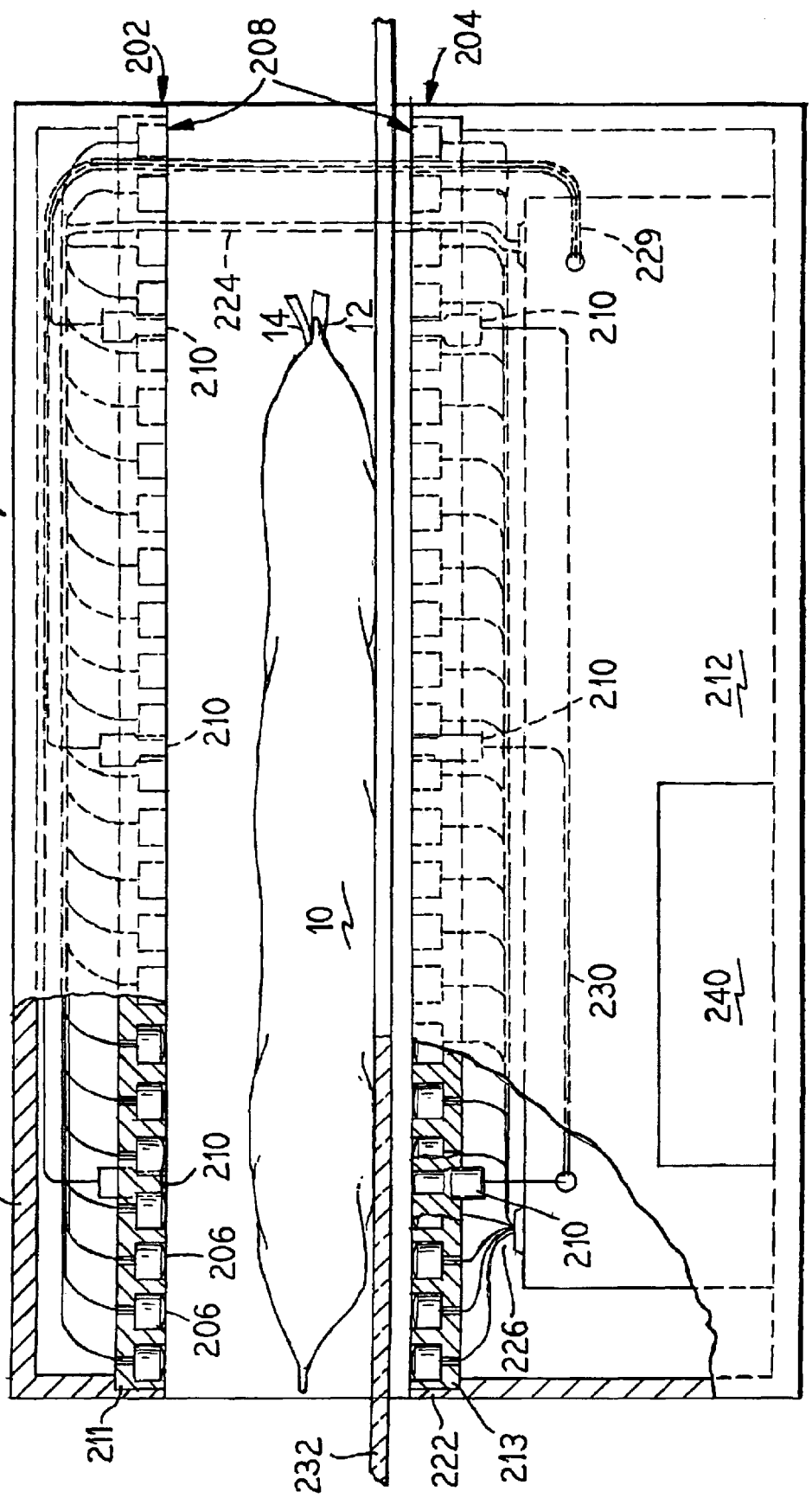

APPARATUS AND METHOD FOR INACTIVATING VIRAL CONTAMINANTS IN BODY FLUIDS

This application is a Continuation of Ser. No. 08/350,398 filed Dec. 6, 1994, no abandoned.

BACKGROUND OF THE INVENTION

The present invention relates generally to apparatus and methods for inactivating viral contaminants that may be present in the body fluids. More specifically, the invention relates to apparatus and methods for photodynamically inactivating viral contaminants in body fluids.

In a variety of therapies, such as transfusions and transplants, body fluids, especially blood components such as red blood cells, platelets, plasma, leukocytes, and bone marrow, are collected from one or more individuals and then infused into a patient. Although such therapies provide treatments, some of which are life saving, due to the transmission of infectious diseases there may be potential risks involved with such therapies.

By way of example, it is known that blood can carry infectious agents such as hepatitis virus, human immunodeficiency virus (an etiological agent for AIDS), and cytomegalovirus. Although screening methods exist to identify blood that may include such viruses, blood containing viruses, and other disease causing pathogens, such as bacteria, cannot be 100% eliminated from the pool of possible blood component supplies. Therefore, there is still a small risk that blood transfusions can transmit viral or other infections.

Accordingly, a goal of recent biomedical research has been to reduce the risk of transmitting an infectious agent by selectively inactivating or depleting pathogens present in such blood components. One approach has been to utilize photosensitive (photoactive) agents that when activated by light of the appropriate wavelength will destroy the ability of the pathogen to cause infection. The use of photodynamic therapy has been suggested as a way to eradicate infectious agents from collected blood and its components prior to storage and/or transfusion.

A number of different photoactive agents have been proposed as possibilities to be used to eradicate viral and other contaminants in body fluids. Such photoactive agents include: psoralens; porphyrins; phthalocyanines; and dyes such as methylene blue. See, for example, U.S. Pat. Nos. 4,748,120; 4,878,891; 5,120,649; and German Patent Application No. DE 39 30 510 A1 (Mohr).

Although much effort has been focussed on commercializing such methods using photoactive agents, the inventors believe that such methods are currently not commercially viable. Even though an ideal system for utilizing a photoactive agent to treat blood to eradicate or remove viral and other contaminants has not been developed, it is envisioned that such a system would entail combining the blood with the photoactive agent in a container and irradiating the resultant mixture with light of the appropriate wavelength.

It is known, of course, to use blood pack units to collect blood. The blood pack units include a container typically constructed from a plastic material, usually a polyvinyl chloride material. The blood pack units are connected to tubes that allow blood to be infused into the container as well as to be accessed therefrom.

Of course, blood pack units must be sterilized. Typically, sterilization takes place by steam sterilization at a temperature of above 100° C. for a predetermined period of time.

One photoactive agent that appears to be promising with respect to eradicating viruses and bacteria from blood is methylene blue. Methylene blue 3-7-bis(dimethylamino) phenothiazine-5-ium chloride ($C_{16}H_{18}ClN_3S$), in the presence of light has been reported to damage DNA and generate singlet oxygen which damages the virus envelop. Accordingly, it can be used to selectively, in a controlled manner, modify the DNA and RNA of bacterial and viral contaminants thereby inactivating the pathogens. See U.S. Pat. No. 4,950,665.

It has recently been determined, however, that if methylene blue is placed into a standard blood pack unit constructed from PVC under standard conditions and the unit is then heat sterilized, that at least a certain amount of the methylene blue migrates into the PVC layer reducing the methylene blue present. The specific amount of methylene blue that migrates is variable depending upon the conditions. However, envisioned methods of using methylene blue to treat blood and other body fluids require that precise amounts of methylene blue be used.

This unfortunately requires that the blood packs must be sterilized prior to methylene blue being added thereto. This can create logistic problems as well as increase the cost of creating the product. Likewise, during the methylene blue filling process, there is the risk of contaminating the sterilized container.

However, it has recently been discovered that methylene blue can be housed in certain containers, or under certain conditions, and sterilized with the blood pack unit without the methylene blue migrating into the plastic. It has been found that two of the parameters that have a great effect on preventing methylene blue from migrating into the plastic are: the type of plastic; and the pH of the methylene blue solution.

It has been found that methylene blue does not migrate into non-PVC material as well as into PVC material under sterilization conditions. One or more suitable containers providing a steam sterilizable housing for the methylene blue are disclosed in U.S. Pat. No. 6,207,107, filed Sep. 28, 1992, the disclosure of which is fully incorporated herein by reference. The housing includes at least an inner surface, the surface that contacts the methylene blue solution, that is constructed from a non-PVC material.

SUMMARY OF THE INVENTION

The present invention provides a method and apparatus for inactivating viral contaminants in a body fluid. By mixing both methylene blue and the body fluid within a container, and then subjecting the container to a suitable light field under no-flow conditions, viral contaminants can be inactivated.

To this end, in an embodiment the invention provides a method for inactivating viruses in a body fluid, comprising the steps of forming a mixture including a therapeutically effective amount of methylene blue and an amount of a body fluid in a container under sterile conditions, and irradiating the mixture with a light field of a suitable intensity and wavelength for activating the methylene blue for a time sufficient to inactivate viruses in a mixture. During the process, the mixture is maintained in a substantially static state within the container.

In an embodiment of the invention, the body fluid a blood component.

In an embodiment of the invention, the blood component is selected from the group consisting of: plasma, red blood cells, white blood cells, leukocytes, bone marrow, and platelets.

In an embodiment of an invention, the step of forming a mixture comprises the step of adding the methylene blue to a container in which the body fluid is already stored.

In an embodiment of the invention, the step of irradiating includes the step of transporting the mixture in the container along a path of a light field.

In an embodiment, the invention provides the further step of allowing excess methylene blue to leach out into the container after the irradiation step.

In an embodiment of the invention, the light field is generated by an array of light emitting diodes.

In an embodiment, the invention provides an apparatus for inactivating at least viruses in a body fluid with methylene blue. The apparatus comprises at least one light source disposed along a path of travel and configured to generate a light field on the path of travel with a frequency suitable for activating methylene blue while not adversely effecting body fluids. The apparatus also includes a transport associated with the light source and configured to transport a container enclosing a mixture of the body fluid and a therapeutically effective amount of the methylene blue along the path of travel and within the light field generated by the light source.

In an embodiment of the invention, the light source comprises a light emitting diode.

In an embodiment of the invention, the light emitting diode light source generates a light field with a wavelength of about 670 nm.

In an embodiment of the invention, the light source comprises an array of light emitting diodes.

In an embodiment of the invention, the transport is configured to transport the container within the light field for at least 5 minutes.

In an embodiment, the invention provides a method for inactivating viruses in a body fluid, comprising the steps of forming a mixture of the body fluid and an effective amount of methylene blue in a container under sterile conditions; and irradiating a mixture with a light field generated by an array of light emitting diodes for a duration sufficient to activate the methylene blue such that the mixture can remain substantially static within the container.

An advantage of the present invention is to provide a method for inactivating viral contaminants in body fluids.

Additional features and advantages of the present invention are described in, and will be apparent from, the detailed description of the presently preferred embodiments and from the drawings.

BRIEF DESCRIPTION OF THE DRAWINGS

FIG. 2 illustrates a fragmentary cross section of the device of FIG. 1.

DETAILED DESCRIPTION OF THE PRESENTLY PREFERRED EMBODIMENTS

Figure 3:
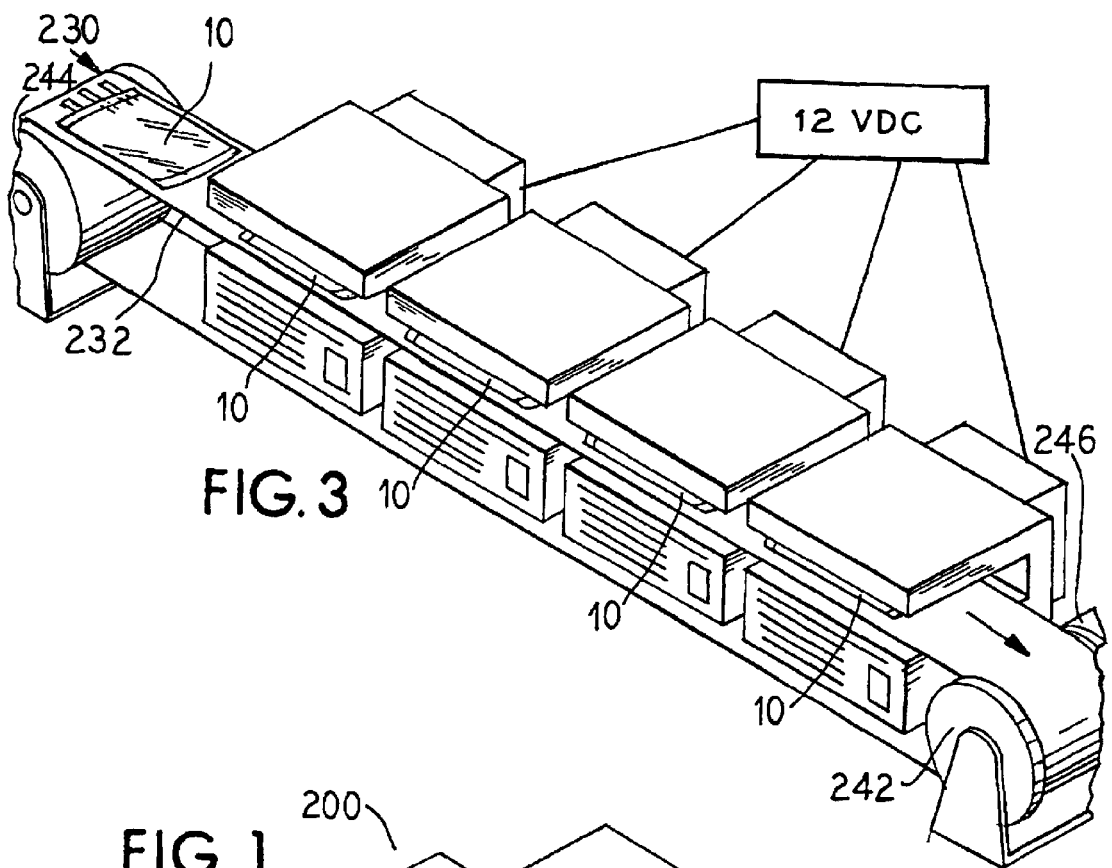
FIG. 3 illustrates a system for irradiating a container with a light field and transporting the container through the light field.

The present invention provides apparatus and methods for inactivating pathogens that may be contained in the body fluids. As used herein, body fluid not only includes blood and its components, but also includes other fluids contained in the body such as blood components, leukocytes, red blood cells, white blood cells, plasma (even fresh frozen), etc., bone marrow, semen, or fluid containing structures such as internal organs.

As previously noted, although body fluids, such as blood and its components, can be used in many therapeutic applications, there is the danger of the transfer of infectious disease due to viral and bacterial contaminants that may be contained in such fluids. Recently the use of photoactive agents has provided the hope of inactivating viral and bacterial contaminants that may be contained in such fluids. However, in order to commercialize such methods, certain obstacles must be overcome.

It is known to house blood components in plastic containers. Typically, the plastic container comprises a polyvinyl chloride structure that is plasticized with di(2-ethylhexyl)phthalate (DEHP) and includes stabilizers. Blood components are stored particularly well in such containers. However, it has been found that when a solution of methylene blue, a photoactive agent of promise, is placed in such a container at a physiological pH of around 7, that upon steam sterilization, the photoactive agent (methylene blue) migrates into the plastic.

Methods of use of methylene blue to inactivate viral contaminants require rather precise amounts of methylene blue. See, for example, Lambrecht, et al., *Photoinactivation of Viruses in Human Fresh Plasma by Phenothiazine Dyes in Combination with Visible Light*, Vox Sang 1991; 60:207–213. Therefore, the migration of the methylene blue solution into the plastic during the sterilization process are believed to provide an unacceptable system.

It has also been found that the migration of methylene blue into the plastic is dependent on a couple of controllable parameters. Therefore, it is possible to provide apparatus and systems wherein methylene blue can be contained within a plastic structure, the structure can be steam sterilized, and the methylene blue solution will be recovered in sufficient quantity to allow the solution to be used to inactivate viral contaminants in a body fluid.

By controlling the type of plastic from which the housing that contains the methylene blue is constructed, the migration of methylene blue into the housing can be controlled. In this regard, it has been found that if at least the layer of the container that contacts the methylene blue is constructed from a non-PVC material, the methylene blue stored therein will not substantially migrate into the plastic.

Although it is envisioned that with proper controls of other parameters, any non-PVC plastic material can be used, of most interest are the more inert plastics, such as polyolefins and polyurethanes. In a preferred embodiment, polypropylene, styrene-ethylene-butylene-styrene (SEBS), ethylenevinyl acetate, and polyesters are used.

By way of example, referring first to FIG. 2, a container 10 is illustrated. The container 10 includes ports 12 and 14 extending therefrom to provide access to an interior of the container 10.

In the container 10 illustrated, the ports 12 and 14 extend from the container 10 and provide means for infusing the body fluid, such as blood or blood components, into the container 10. An example of a system that can be used is the Optipak® system that is disclosed in U.S. Pat. No. 4,608,178. In this system, plasma or red blood cells, for example, can be infused into the container 10 through the ports after having been separated from whole blood.

The container 10 can have a structure that is substantially similar to the container for housing blood and blood components available from the Fenwal Division of Baxter International Inc. However, the container 10 can also be constructed so that at least an interior layer that defines the interior surface of the container is constructed from a non-PVC material so as to house methylene blue alone. In that case, most preferably, at least the inner surface of the container 10 is constructed from SEBS, polypropylene, polyester, polyurethane, or ethylenevinyl acetate, or blends thereof. Of course, if desired, the entire container 10 can be constructed from a non-PVC material.

Pursuant to the present invention, a body fluid such as a blood component and a therapeutically effective amount of methylene blue are mixed together in the container 10. In one embodiment, the methylene blue is added to body fluid already stored in the container 10. In another embodiment, the body fluid is added to a therapeutically effective amount of methylene blue already stored in the container 10. The foregoing can be accomplished by any known sterile means and/or method that has been found to function satisfactorily. In this embodiment, the amount of methylene blue solution used is about 10 ml.

It has been found that the pH of the solution can effect the migration of the solution into the plastic material during sterilization. Preferably, the methylene blue solution has been adjusted to a pH of less than 7.0 and most preferably approximately 6.3 or less.

Pursuant to the present invention, if methylene blue solution is initially infused into the container 10, the container 10 and methylene blue solution can then be steam sterilized, e.g., at 115° C. for 65 minutes. Due to the use of a methylene blue solution having a pH of less than 7.0 and the fact that the container 10 would then include at least an inner surface that is constructed from a non-PVC material, the methylene blue solution, during steam sterilization, will not substantially migrate into the plastic.

A body fluid, such as a blood component, can then be infused into the container 10 through port 14 or 12. To control fluid flow through the port, a breakable cannula or other means can be used.

In the container 10, the body fluid, preferably a blood component, will mix with the methylene blue solution. The container 10 is then irradiated by a light field of the appropriate wavelength (approximately 620–670 nm) to activate the methylene blue within the container 10. This will cause the methylene blue to inactivate any pathogens, e.g., viruses and bacteria, that are contained within the blood component, thus insuring a blood component that does not contain pathogens. Preferably, the mixture is inactivated for a sufficiently long period of time and at a suitable wavelength to inactivate at least substantially all the viruses in the mixture.

Figure 1:
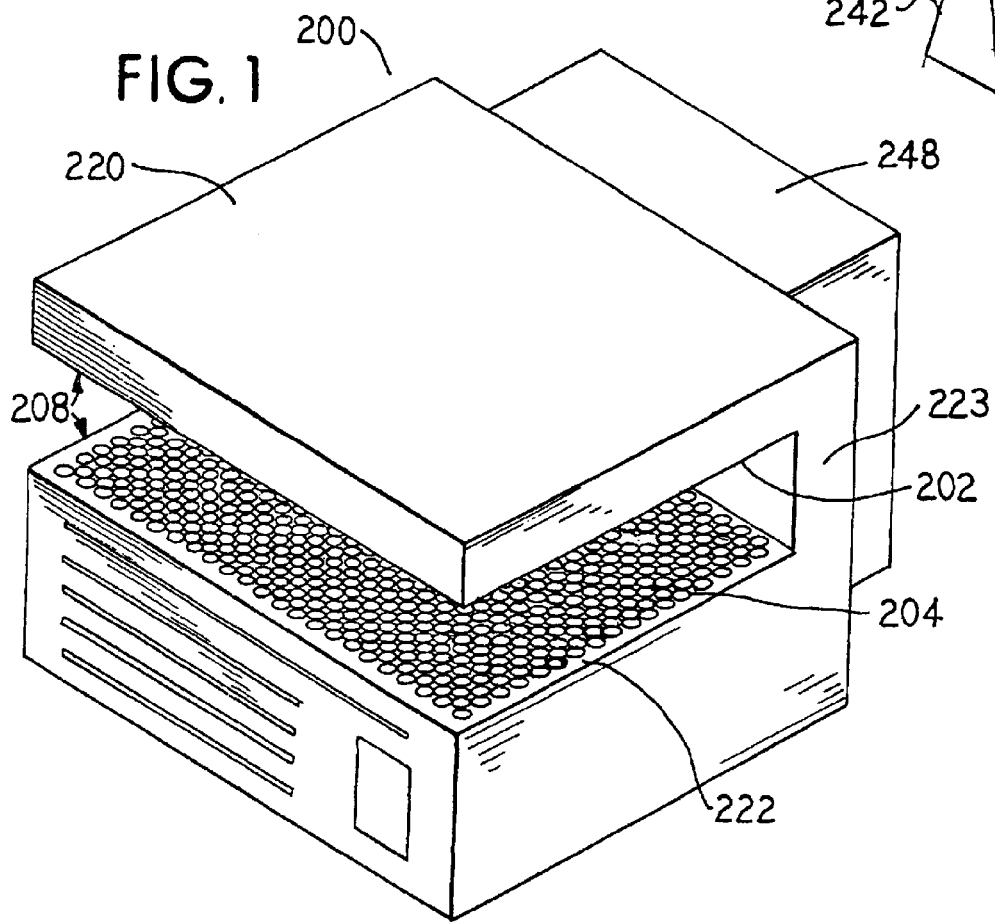
FIG. 1 illustrates a perspective view of a device for irradiating a container with a light field.

Referring now to both FIGS. 1 and 2, there is illustrated an apparatus 200 for generating the appropriate light field. As illustrated, the apparatus 200 preferably includes facing arrays 202 and 204 of light emitting diodes 206 that generate the light field to which the container 10 can be subjected. As will be appreciated, the apparatus 200 preferably is used for activating methylene blue in single units of fresh frozen plasma.

In an embodiment of the apparatus 200, the light emitting diodes 206 comprise light emitting diodes manufactured by Hewlett Packard under the designation HLMP-8103 and have a light output centered at a wavelength of about 670 nm. Red blood cells are transparent to light radiated at about this wavelength. The methylene blue, however, is not. Instead, at this wavelength the methylene blue absorbs the light and becomes activated.

In an embodiment, the light emitting diodes 206 preferably are mounted onto printed circuit boards 211 and 213 about the size of 8½"×11" sheets of paper. Each board then holds approximately 1280 light emitting diodes forming the relatively large arrays 202 and 204 of light emitting diodes. When powered by a 12 volt DC power supply, the pair 202 and 204 of such arrays can deliver a light field of about 30.0 mw per centimeter square.

As illustrated, in the apparatus 200, the two arrays 202 and 204 are mounted facing each other in spaced apart relation in such a way that a gap 208 is present within which a container containing about 250 ml of the body fluid, preferably fresh frozen plasma, and containing about 1 $\mu$M methylene blue can be placed between the two arrays 202 and 204. The container can then be irradiated for about 5 minutes, which causes the methylene blue therein to inactivate any virus present.

As a result, the methylene blue and body fluid to be treated can be separately collected and sterilized, and then mixed either in the container in which the methylene blue was collected or the container in which the body fluid was collected. Then, the container can be relatively quickly irradiated by the light field generated by the apparatus 200 so that the mixture therein need not be flowed through flow paths and the like past the sources of light.

In an embodiment, the body fluid and methylene blue are contained in a PVC container. Due to the use of a PVC container, excess methylene, i.e., methylene blue that is not activated or necessary for photoinactivation of the viruses, leaches out into the container material. Thus, the body fluid can be relatively quickly treated and excess methylene blue is removed from the body fluid.

As illustrated in FIG. 2, a device such as the apparatus 200 can be equipped with light sensors 210 that can measure how much light is being delivered to the container 10 and how much light is being transmitted through the container 10 to control a total dosage of light. To this end, the apparatus can include a microprocessor based computer 212 that monitors the sensors 210 and computes cumulative dosages of light. Once a sufficient dosage is reached, the computer 212 can shut off the light emitting diodes 206.

It can be appreciated that some body fluids and/or containers are more opaque than other fluids and/or containers and that therefore the computer 212 must adjust the irradiation time to accommodate the different light transmissions through the containers due to the differences in opacities of different body fluids.

As illustrated in FIGS. 1 and 2, in the embodiment illustrated, the apparatus 200 is constructed such that the array 202 is supported within an arm 220 that overhangs a facing support surface 222. The support surface 222 in turn supports or includes the array 204. The overhang 220 is in turn supported by perpendicular wall 223.

Interconnecting lines or cables 224 can be used to interconnect the diodes 206 of the array 202 and the computer 212. Similar lines or cables 226 can be used to interconnect the diodes 206 of the array 204 to the computer 212. In a readily programmable manner, the computer 212 can be used to turn the arrays 202 and 204 off and on as needed.

At the same time, lines or cables can be used to interconnect the sensors 210 in the array 204 with the computer 212. Similarly, lines or cables 229 can be used to interconnect the sensor 210 in the array 202 with the computer 212.

Referring now to FIG. 3, it can be seen that a plurality of such apparatus 200 can be placed along a path of travel defined by, in an embodiment, a conveyor 230. A container can be placed on a belt 232 of the conveyor 230 at one end of the conveyor 230 and transported past successive apparatus 200. It can be appreciated that the speed of the belt 232 can be adjusted. Accordingly, each container 10 placed thereon would be transported by the series of light field apparatus 200 with such a timing (preferably 5 minutes or so) that at the end of the path of travel, the container 10 will have been subjected to a sufficient dosage of light to virally inactivate the body fluid contained therein.

A suitable power supply 240, e.g., a 12 volt DC power supply, can be coupled to each apparatus 200 as illustrated. Moreover, the conveyor 230 can be provided with suitable drive wheels 242 and 244 at opposite ends thereof, as well as a suitably controllable drive motor 246. A fan 248 is provided for cooling the device.

It can be appreciated that the belt 232 of the conveyor 230 should be sufficiently translucent to allow both arrays 202 and 204 to generate the appropriate light field. If the belt 232 is not sufficiently translucent, then the light field could be cut up to half and then the exposure time would have to be suitably increased.

With reference to FIG. 3, it can be appreciated that all of the apparatus 200 can be connected to a single computer, perhaps even only one of the computers 212 such that the single computer monitors the total dosage of light received by each container 10 passing through the light field. The programming necessary to effect the foregoing is minimal and well within the capabilities of one of ordinary skill in the art, and therefore it is believed to not be necessary to set forth such programming herein.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A method for inactivating viruses in a blood or blood component, the method comprising the steps of:
   initially storing an amount of methylene blue and an amount of the blood or blood component in separate sterile containers, each container having an inner surface made of a non-polyvinyl chloride, plastic material and the container in which the blood or blood component is stored includes portions that are made of a polyvinyl chloride material;
   forming a mixture by adding at least a portion of the amount of the methylene blue to the amount of the blood or blood component wherein the portion of methylene blue is a virucidally effective amount of the methylene blue and further wherein the mixture formed is within one of the containers in which the methylene blue or blood or blood component is initially stored under sterile conditions; and
   irradiating the mixture with a light field of a suitable intensity and wavelength for activating the methylene blue for a time sufficient to inactivate viruses in the mixture, while maintaining the mixture under a substantially no flow condition within the container in which the mixture is formed.

2. The method of claim 1 wherein the blood component is selected from the group consisting of: plasma, red blood cells, white blood cells, and platelets.

3. The method of claim 1 further comprising the step of: adding the methylene blue to the container in which the blood or blood component is already stored.

4. The method of claim 1 further comprising the step of: adding the blood or blood component to the container that contains methylene blue.

5. The method of claim 1 further comprising the step of: transporting the mixture in the container in which the mixture is formed on a conveyor past at least two light sources.

6. The method of claim 1 wherein the light field is generated by at least one array of light emitting diodes.

7. The method of claim 1 wherein the mixture is irradiated by the light field for a cumulative period of at least five minutes.

8. A method for inactivating viruses in a blood or blood component, the method comprising the steps of:
   initially storing an amount of methylene blue having a pH of less than 7.0 in a container that includes an interior and at least one port extending from the container that provides controlled access to the interior, the container is constructed of a plastic material and includes an inner surface made of a non-polyvinyl chloride, plastic material;
   forming a mixture by adding at least a portion of the amount of the methylene blue to an amount of the blood or blood component, by use of the port, wherein the portion of methylene blue is a virucidally effective amount of the methylene blue and further wherein the mixture formed is within either the container or in a second container that initially housed the blood or blood components; and
   irradiating the mixture with a light field of a suitable intensity and wavelength for activating the methylene blue for a time sufficient to inactivate viruses in the mixture, while maintaining the mixture under a substantially no flow condition within the container in which the mixture is formed.

9. The method of claim 8 wherein the blood component is selected from the group consisting of: plasma, red blood cells, white blood cells, and platelets.

10. The method of claim 8 further comprising the step of: adding the methylene blue to the second container in which the blood or blood component is housed.

11. The method of claim 8 wherein the container in which the mixture is formed includes a polyvinyl chloride material.

12. The method of claim 8, wherein the light field is generated by at least one array of light emitting diodes.

13. The method of claim 8 wherein the mixture is irradiated by the light field for a cumulative period of at least five minutes.

14. A method for inactivating viruses in a blood or blood component, the method comprising the steps of:
   initially storing an amount of methylene blue in a container that includes an interior and at least one port extending from the container that provides controlled access to the interior, the container is constructed of a plastic material and includes an inner surface made of a non-polyvinyl chloride, plastic material;
   forming a mixture bv adding at least a portion of the amount of the methylene blue to an amount of the blood or blood component, by use of the port, wherein the portion of methylene blue is a virucidally effective amount of the methylene blue and further wherein the mixture formed is within either the container or in a second container that initially housed the blood or blood component;
   irradiating the mixture with a light field of a suitable intensity and wavelength for activating the methylene blue for a time sufficient to inactivate viruses in the mixture, while maintaining the mixture under a substantially no flow condition within the container in which the mixture is formed;

wherein the container in which the mixture is formed does not include any polyvinyl chloride plastic.

15. A method for inactivating viruses in a blood or blood component, the method comprising the steps of:

initially storing an amount of methylene blue in a container that includes an interior and at least one port extending from the container that provides controlled access to the interior, the container is constructed of a plastic material and includes an inner surface made of a non-polyvinyl chloride, plastic material;

forming a mixture by adding the blood or blood component to the container that contains methylene blue, by use of the port, wherein the portion of methylene blue is a virucidally effective amount of the methylene blue; and irradiating the mixture with a light field of a suitable intensity and wavelength for activating the methylene blue for a time sufficient to inactivate viruses in the mixture, while maintaining the mixture under a substantially no flow condition within the container in which the mixture is formed.

16. A method for inactivating viruses in a blood or blood component, the method comprising the steps of:

initially storing an amount of methylene blue in a container that includes an interior and at least one port extending from the container that provides controlled access to the interior, the container is constructed of a plastic material and includes an inner surface made of a non-polyvinyl chloride, plastic material;

forming a mixture by adding at least a portion of the amount of the methylene blue to an amount of the blood or blood component, by use of the port, wherein the portion of methylene blue is a virucidally effective amount of the methylene blue and further wherein the mixture formed is within either the container or in a second container that initially housed the blood or blood component; and irradiating the mixture with a light field of a suitable intensity and wavelength for activating the methylene blue for a time sufficient to inactivate viruses in the mixture, while maintaining the mixture under a substantially no flow condition within the container in which the mixture is formed;

wherein the container in which the mixture is formed comprises at least an inner surface made of a non-polyvinyl chloride material.

17. A method for inactivating viruses in a blood or blood component the method comprising the steps of:

initially storing an amount of methylene blue in a container that includes an interior and at least one port extending from the container that provides controlled access to the interior, the container is constructed of a plastic material and includes an inner surface made of a non-polyvinyl chloride, plastic material;

forming a mixture by adding at least a portion of the amount of the methylene blue to an amount of the blood or blood component, by use of the port, wherein the portion of methylene blue is a virucidally effective amount of the methylene blue and further wherein the mixture formed is within either the container or in a second container that initially housed the blood or blood component;

transporting the mixture in the container in which the mixture is formed on a conveyor past at least two light sources; and irradiating the mixture with a light field of a suitable intensity and wavelength for activating the methylene blue for a time sufficient to inactivate viruses in the mixture, while maintaining the mixture under a substantially no flow condition within the container in which the mixture is formed.

18. A method for inactivating viruses in a blood or blood component, the method comprising the steps of:

initially storing an amount of methylene blue in a container that includes an interior and at least one port extending from the container that provides controlled access to the interior, the container is constructed of a plastic material and includes an inner surface made of a non-polyvinyl chloride, plastic material;

forming a mixture by adding at least a portion of the amount of the methylene blue to an amount of the blood or blood component, by use of the port, wherein the portion of methylene blue is a virucidally effective amount of the methylene blue and further wherein the mixture formed is within either the container or in a second container that initially housed the blood or blood component;

allowing excess methylene blue to leach into the container in which the blood or blood component is stored after mixture with the methylene blue; and irradiating the mixture with a light field of a suitable intensity and wavelength for activating the methylene blue for a time sufficient to inactivate viruses in the mixture, while maintaining the mixture under a substantially no flow condition within the container in which the mixture is formed.

* * * * *